US010857329B2

(12) United States Patent
Davies et al.

(10) Patent No.: US 10,857,329 B2
(45) Date of Patent: Dec. 8, 2020

(54) COLLAPSIBLE TIP RE-ENTRY CATHETER

(71) Applicant: Baylis Medical Company Inc., Montreal (CA)

(72) Inventors: Gareth Davies, Toronto (CA); Anna Strachan, Toronto (CA); Linus Leung, Toronto (CA); Yun Uhm, Toronto (CA)

(73) Assignee: Baylis Medical Company Inc., Mississauga (CA)

( * ) Notice: Subject to any disclaimer, the term of this patent is extended or adjusted under 35 U.S.C. 154(b) by 208 days.

(21) Appl. No.: 15/214,084

(22) Filed: Jul. 19, 2016

(65) Prior Publication Data

US 2016/0325073 A1    Nov. 10, 2016

Related U.S. Application Data

(63) Continuation of application No. PCT/IB2015/050396, filed on Jan. 19, 2015.
(Continued)

(51) Int. Cl.
*A61M 25/00* (2006.01)
*A61B 17/3207* (2006.01)
(Continued)

(52) U.S. Cl.
CPC ... *A61M 25/008* (2013.01); *A61B 17/320783* (2013.01); *A61F 2/844* (2013.01);
(Continued)

(58) Field of Classification Search
CPC .. A61M 2025/0025; A61M 2025/0183; A61M 25/0021; A61M 25/005;
(Continued)

(56) References Cited

U.S. PATENT DOCUMENTS

| 2,116,083 A | 5/1938 | Rusch |
| 4,531,943 A | 7/1985 | Van Tassel et al. |

(Continued)

FOREIGN PATENT DOCUMENTS

| EP | 2574364 A1 | 4/2013 |
| WO | 1999048544 A1 | 9/1999 |

(Continued)

OTHER PUBLICATIONS

European Patent Office Supplementary Search Report, European Application No. 15737506.4, dated Jan. 15, 2018.
(Continued)

*Primary Examiner* — Quynh-Nhu H. Vu
(74) *Attorney, Agent, or Firm* — Glenn Arnold; Vincent Man; Samuel Tekie

(57) ABSTRACT

A method and apparatus are disclosed for a catheter having a side-port through which a wire may be advanced. The catheter comprises a catheter body, the catheter body defining at least a primary catheter lumen and at least one side-port in communication with the primary catheter lumen, and a distal portion of the catheter extending distal to the at least one side-port, the side-port being configured to allow travel of a wire or other component therethrough, wherein the distal portion of the catheter is radially collapsible.

13 Claims, 7 Drawing Sheets

Related U.S. Application Data

(60) Provisional application No. 61/932,891, filed on Jan. 29, 2014, provisional application No. 61/929,158, filed on Jan. 20, 2014.

(51) Int. Cl.
*A61F 2/844* (2013.01)
*A61M 25/01* (2006.01)
*A61L 29/14* (2006.01)
*A61L 29/06* (2006.01)
*A61B 17/32* (2006.01)

(52) U.S. Cl.
CPC .............. *A61L 29/06* (2013.01); *A61L 29/14* (2013.01); *A61M 25/005* (2013.01); *A61M 25/007* (2013.01); *A61M 25/0021* (2013.01); *A61M 25/0054* (2013.01); *A61M 25/0108* (2013.01); *A61M 25/0169* (2013.01); *A61B 2017/320056* (2013.01); *A61M 2025/0025* (2013.01); *A61M 2025/0183* (2013.01)

(58) Field of Classification Search
CPC ............ A61M 25/0054; A61M 25/007; A61M 25/008; A61M 25/0108; A61M 25/0169
See application file for complete search history.

(56) References Cited

U.S. PATENT DOCUMENTS

| | | | | |
|---|---|---|---|---|
| 4,552,554 A | * | 11/1985 | Gould | A61M 25/01 604/104 |
| 4,774,949 A | | 10/1988 | Fogarty | |
| 5,205,830 A | | 4/1993 | Dassa | |
| 5,447,503 A | * | 9/1995 | Miller | A61M 25/0068 604/528 |
| 5,531,685 A | | 7/1996 | Hemmer | |
| 5,637,091 A | | 6/1997 | Hakky et al. | |
| 6,183,443 B1 | * | 2/2001 | Kratoska | A61B 17/3439 604/164.01 |
| 6,312,374 B1 | * | 11/2001 | von Hoffmann | A61M 25/104 600/3 |
| 6,358,238 B1 | * | 3/2002 | Sherry | A61M 25/0023 604/524 |
| 6,821,287 B1 | * | 11/2004 | Jang | A61M 25/0023 604/160 |
| 6,951,555 B1 | | 10/2005 | Suresh et al. | |
| 7,004,173 B2 | | 2/2006 | Sparks et al. | |
| 7,037,293 B2 | * | 5/2006 | Carrillo | A61B 1/018 604/103.04 |
| 7,087,053 B2 | | 8/2006 | Vanney | |
| 7,785,314 B2 | | 8/2010 | Miller et al. | |
| 8,285,362 B2 | | 10/2012 | Dietz et al. | |
| 8,460,239 B2 | * | 6/2013 | Jordan | A61F 2/95 604/103.04 |
| 8,603,035 B2 | * | 12/2013 | Schwager | A61M 25/0172 604/160 |
| 8,801,749 B2 | * | 8/2014 | Adams | A61F 2/013 606/200 |
| 2001/0000041 A1 | * | 3/2001 | Selmon | A61B 17/3207 600/585 |
| 2002/0142119 A1 | | 10/2002 | Seward | |
| 2003/0032936 A1 | | 2/2003 | Lederman | |
| 2003/1999849 | | 10/2003 | Hackett | |
| 2004/0260271 A1 | | 12/2004 | Huyser | |
| 2006/0142703 A1 | * | 6/2006 | Carter | A61M 25/0052 604/264 |
| 2007/0197856 A1 | | 8/2007 | Gellman et al. | |
| 2009/0018502 A1 | * | 1/2009 | Reifart | A61M 25/104 604/103.04 |
| 2009/0118661 A1 | | 5/2009 | Moehle | |
| 2009/0209941 A1 | | 8/2009 | Aggerholm et al. | |
| 2009/0270800 A1 | | 10/2009 | Spurchise et al. | |
| 2009/0270802 A1 | | 10/2009 | Nishide et al. | |
| 2010/0106237 A1 | | 4/2010 | Webster | |
| 2012/0123258 A1 | | 5/2012 | Willard | |
| 2013/0006173 A1 | | 1/2013 | Alvarez et al. | |
| 2013/0158507 A1 | * | 6/2013 | Brown | A61M 25/007 604/506 |
| 2013/0197353 A1 | * | 8/2013 | Von Oepen | A61M 25/0009 600/424 |
| 2013/0331782 A1 | * | 12/2013 | Grovender | A61M 25/0045 604/103.04 |

FOREIGN PATENT DOCUMENTS

| | | |
|---|---|---|
| WO | 2009006145 A1 | 4/2010 |
| WO | 20110133513 A3 | 10/2011 |
| WO | 20120009187 A1 | 1/2012 |

OTHER PUBLICATIONS

Patent Cooperation Treaty, International Search Report and Written Opinion of the International Searching Authority for International Application No. PCT/IB2015/050396, dated Jul. 9, 2015.

Patent Cooperation Treaty, Preliminary Report on Patentability, for International Application No PCT/IB2015/050396, dated Jul. 26, 2016.

European Patent Office Supplementary Search Report, European Application No. 15743285.7, dated Aug. 29, 2017.

* cited by examiner

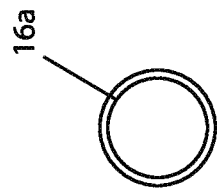
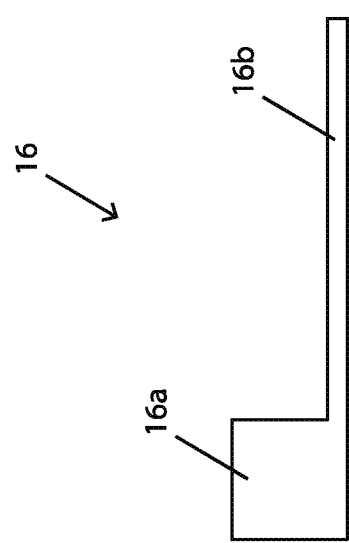

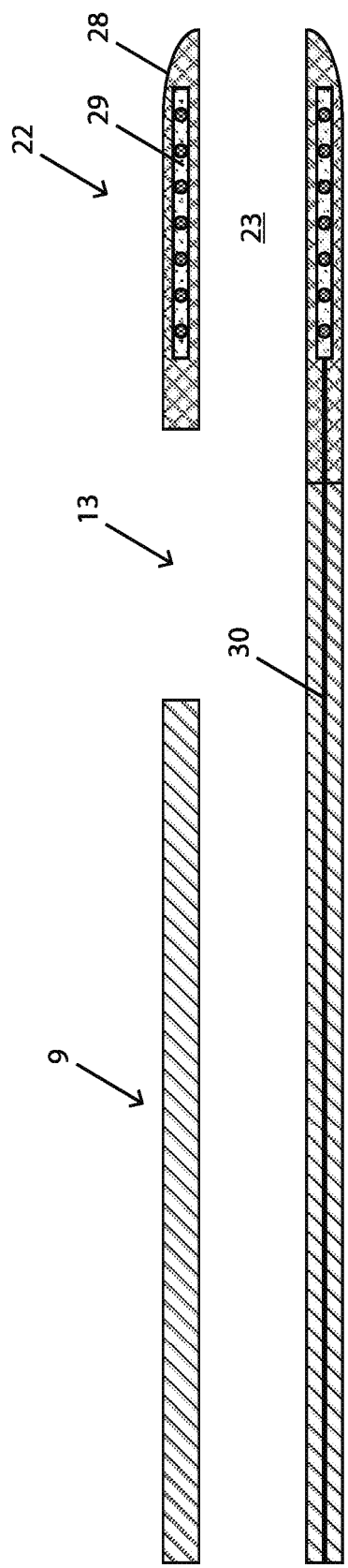

COLLAPSIBLE TIP RE-ENTRY CATHETER

CROSS-REFERENCES TO RELATED APPLICATIONS

This application claims the benefit of the filing date of U.S. Provisional Application Ser. No. 61/929,158, filed Jan. 20, 2014, entitled "Collapsible Tip Re-entry Catheter", the entire disclosure of which is hereby incorporated by reference into the present disclosure. This application also incorporates by reference U.S. Provisional Application Ser. No. 61/932,891, filed Jan. 29, 2014, entitled "Side-port Catheter"

TECHNICAL FIELD

The disclosure relates to the field of medical devices, and in particular relates to the field of catheters.

SUMMARY

In some procedures, there is a problem withdrawing a catheter that has a wire extended out of a side-port of the catheter when the wire is pushed into the side of the catheter distal of the side-port such that there is not enough space (or too much friction between the wire and catheter) to retract the catheter while maintaining wire position. The problem may be addressed by a catheter disclosed herein which is sufficiently radially collapsible distal of the side-port to yield to the wire such that there is enough space to withdraw the catheter without altering the position of the wire within a patient's body.

In one broad aspect, embodiments of the present invention include a catheter comprising a catheter body, the catheter body defining at least a primary catheter lumen and at least one side-port in communication with the primary catheter lumen, a distal portion of the catheter extending distal to the at least one side-port, the side-port being configured to allow travel of a device (a wire or other component) therethrough, wherein the distal portion of the catheter is radially collapsible.

As a feature of this broad aspect, the distal portion of the catheter body is operable to collapse inwardly into the primary catheter lumen and thereby temporarily adopt a reduced profile in a collapsed configuration when force is applied to an outer surface of the distal portion of the catheter body.

As a feature of other embodiments of this broad aspect, the distal portion of the catheter body is operable to collapse inwardly into the primary catheter lumen, and thereby temporarily adopt a reduced profile in a collapsed configuration, when a controlled force is applied to the distal portion of the catheter body.

BRIEF DESCRIPTION OF THE DRAWINGS

In order that the invention may be readily understood, embodiments of the invention are illustrated by way of examples in the accompanying drawings, in which:

FIG. 3 is a side cutaway view of an embodiment of a marker;

FIG. 4 is an end cutaway view of the marker of FIG. 3;

FIG. 7 is a side cutaway view of another alternative embodiment of the catheter having a shape memory element.

DETAILED DESCRIPTION

Figure 1:
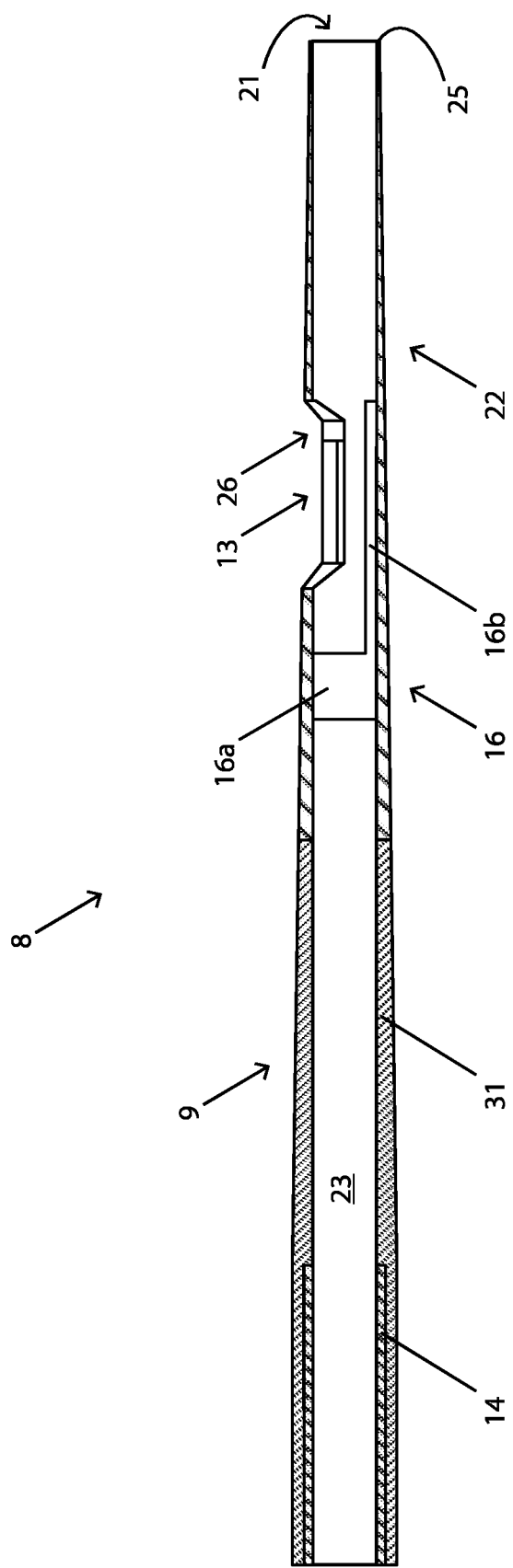
FIG. 1 is a cut away view of a distal portion of an embodiment of a catheter.

A surgical procedure, such as, for example, a percutaneous transluminal angioplasty (PTA) of a challenging occlusion, may include a guide-wire being advanced and taking a sub-intimal path, intentionally or unintentionally. A physician has the option of using a re-entry catheter with a side-port to gain access to the true lumen (i.e. the lumen of the elongated vessel containing the occlusion) distal of the occlusion. There is more than one way to gain access to the true lumen using a side-port of a re-entry catheter. For example, the catheter could be a deflecting catheter that deflects an advancing wire, or alternatively, a directable/steerable wire (e.g. an angled guide-wire) could be directed through a passive side-port (i.e. the side-port of a non-deflecting catheter). The advancing wire may have a sharp tip for cutting, or alternatively, it may have an atraumatic tip with an electrode for delivering energy for puncturing.

Once access to a true lumen has been gained, a wire advanced into the true lumen may be used as a rail to advance devices, such as balloons or stents, into the true lumen. Prior to using a wire that has been advanced from the sub-intimal space into the true lumen as a rail, the re-entry catheter is typically withdrawn while avoiding pulling the wire back into the sub-intimal space.

Withdrawing a catheter that has a wire extended out of a side-port of the catheter poses a challenge when the wire and catheter are contained in a region of tissue, lumen or other structure where movement is restricted. For example, when withdrawing a catheter having a wire extended through a side-port thereof, while retaining a position of the wire in a tissue, a portion of the catheter distal to the side-port is retracted alongside the wire. In some such situations, unhindered retraction of the catheter is prevented due to the structure through which the catheter has been positioned, i.e. there are limited, if any, gaps between the outer surface of the catheter and the surrounding structure. Under such circumstances, as the catheter is retracted, the wire extending through the side-port is forced against the outer surface of the portion of the catheter distal of the side-port whereby friction between the wire and catheter may cause the catheter to pull the wire out of position.

Challenges such as described above may occur, for example, in a lumen having a diameter less than the total of the catheter outer diameter and the wire outer diameter, whereby there is insufficient space to allow for unimpeded or unhindered retraction of the catheter alongside the wire. In one specific example, a re-entry catheter has a profile that is too large for it to be withdrawn through a 6F introducer while maintaining the wire position. Alternatively, such challenges may occur when the re-entry catheter is positioned sub-intimally through a vessel wall.

As will be further described hereinbelow, the present inventors have conceived of and reduced to practice an embodiment of a catheter configured to be sufficiently radially collapsible or deformable distal of the side-port in order to yield to forces applied thereto, for example by a wire positioned alongside, to thereby adopt a reduced profile distal of the side-port. Such an embodiment allows for reduced friction between the wire and catheter, which in turn enables withdrawal or retraction of the catheter while avoiding significantly altering the position of the wire.

In some such embodiments, the radially collapsible or deformable portion of the disclosed catheter is able to temporarily adopt a lower or reduced profile without any direct user control of collapsibility. In such embodiments, the radially collapsible portion of the catheter distal of the side-port may be described as having passive collapsibility or passive radial flexibility.

In some alternative embodiments, the distal portion of the catheter body is operable to collapse inwardly into the primary catheter lumen, and thereby temporarily adopt a reduced profile in a collapsed configuration, when a controlled force (i.e. a force controlled by a user) is applied to the distal portion of the catheter body. In such embodiments, the radially collapsible portion of the catheter distal of the side-port may be described as having controlled or active collapsibility.

Typically, embodiments of the disclosed catheter are used in a sheath and the sheath defines the lumen containing the catheter. In alternative applications, embodiments of the catheter are used without a sheath, or advanced forward of a sheath whereby an anatomical feature, such as a vessel wall, defines the structure containing the catheter.

Figure 5:
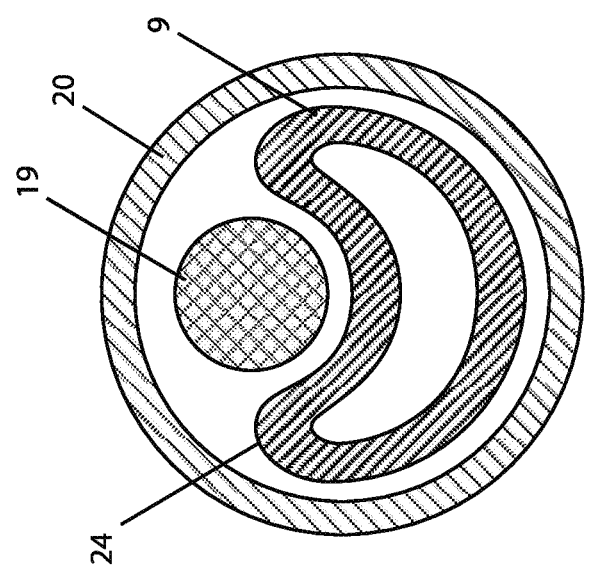
FIG. 5 is a cross-sectional view of the sheath of FIG. 8 containing a catheter and wire.
Figure 8:
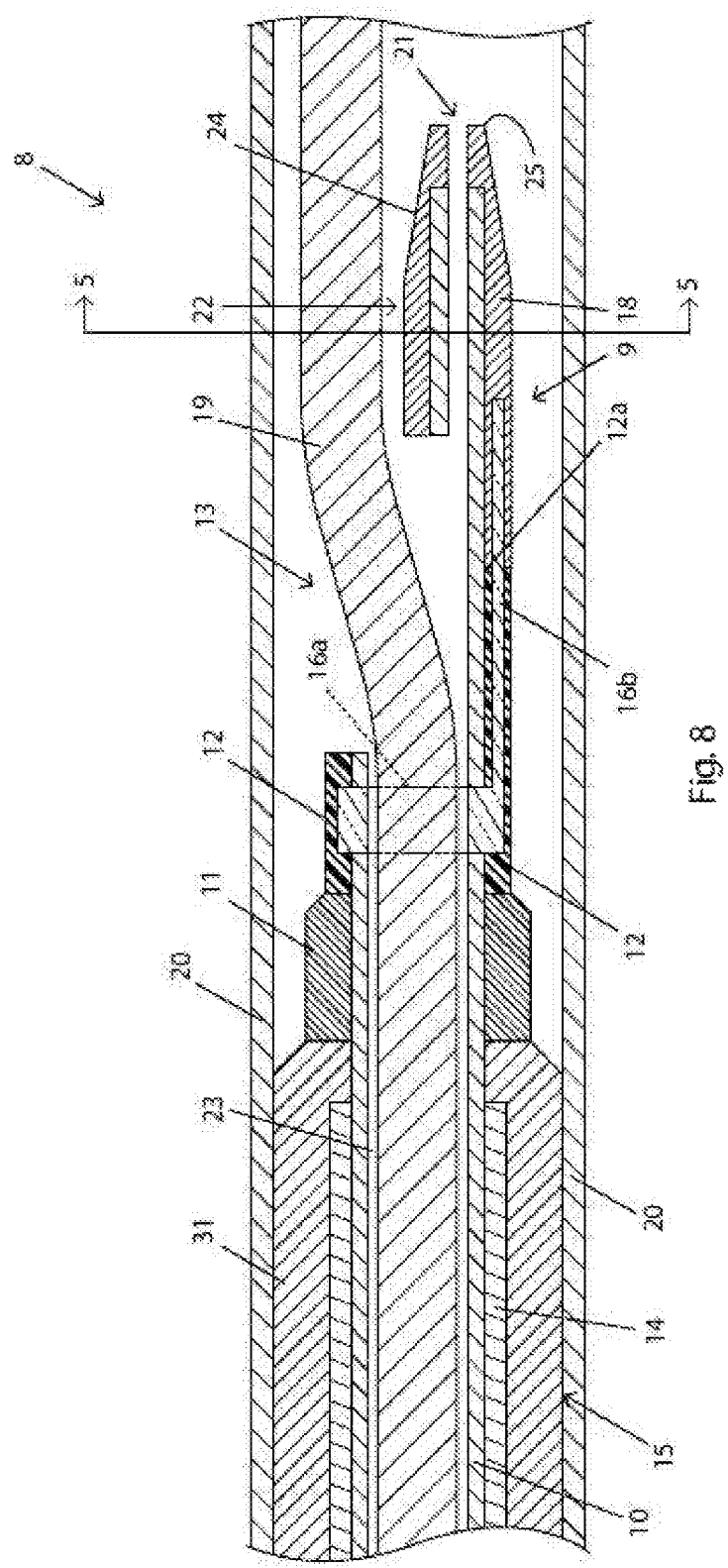
FIG. 8 is a diagrammatic cut away view of a distal portion of the embodiment of catheter of FIG. 2 in a collapsed configuration inside of a sheath.

An exemplary embodiment is illustrated in FIG. 5, which is a cross-sectional cut of catheter 8 along cut line 5-5 in FIG. 8. FIG. 5 shows a cross-sectional view of a sheath 20 containing a catheter body 9 and a wire 19 that has previously been advanced through a side-port of the catheter. When a wire has been advanced through the side-port of a catheter defining a lumen, the portion of the catheter lumen distal to the side-port is understood to be "empty" i.e. the wire is absent from that portion of the catheter. FIG. 5 illustrates wire 19 pressing against the side of the catheter 8 as the catheter is being withdrawn through sheath 20 whereby the illustrated portion of catheter 8 (i.e. the portion distal of the side-port) is collapsed or deformed. The collapsible nature of this portion of the catheter assists in reducing friction between the wire 19 and catheter 8, thereby ensuring that a position of the wire within the true lumen is substantially maintained. In the context of the present invention, and as would be understood by one skilled in the art, it is acceptable for wire 19 to be withdrawn a limited distance as catheter 8 is retracted, so long as a distal end of wire 19 remains in the true lumen whereby the wire is operable to function as a bridge or rail for advancing devices thereover.

In some particular embodiments, the portion of the catheter distal of the side-port is collapsible when a guide-wire is absent from a lumen defined therethrough, i.e. when it is not containing a guide-wire (or another type of wire or wire-shaped device), but retains a non-collapsed or non-deformed configuration when housing a wire or other structure therein.

In some embodiments, the distal tip of the catheter defines a distal end opening or aperture whereby the catheter is operable to be advanced over the guide-wire as an over-the-wire device, or alternatively, a guide-wire may be advanced or withdrawn through the distal end opening of the catheter. As noted above, in some such embodiments, when the portion of the catheter distal of the side-port contains a wire, the wire provides structural (radial) support to the catheter, whereby the distal portion of the catheter housing the wire is operable (has sufficient column strength) to be advanced over the wire and through the anatomy of a patient without ovalization of the catheter, i.e. the catheter retains a non-collapsed configuration.

Thus, the present inventors have conceived and reduced to practice a collapsible tip catheter with a side-port that may be used for re-entry procedures or for advancing into bifurcations. The catheter is sufficiently radially collapsible distal of the side-port whereby it has a collapsed configuration which allows he catheter to be withdrawn without altering the position of a wire which is extending through the side-port.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

FIG. 1 illustrates an embodiment of a catheter 8 including a catheter body 9 defining a lumen 23 (a primary catheter lumen), a side-port 13 in fluid communication with lumen 23, a distal portion 22 of catheter body 9, a distal tip 25 defining an end opening 21 which is in fluid communication with lumen 23, and a marker 16. Distal portion 22 is the portion of catheter body 9 distal of side-port 13. The marker 16 of FIG. 1 includes a marker band 16a and a marker backbone 16b. In the illustrated embodiment, marker band 16a is proximal of side-port 13, and marker backbone 16b is substantially parallel and opposite to side-port 13. Side-port 13 is typically elongated. A wire braid layer 14, shown in the left side of the drawing, ends proximally of side-port 13. Wire braid layer 14 is covered by proximal sleeve 31. The embodiment of FIG. 1 includes side-port 13 located in a recess 26 in the outer surface 24 of the catheter, unlike the embodiment of FIG. 2 (described below) which does not include a recess. In some embodiments, side-port 13 is capsule-shaped, having a straight elongate portion with a length about 0.1420±0.01 inches (3.61±0.254 mm) and curved end portions, each with a radius of about 0.0200±0.002 inches (0.508±0.051 mm). Some embodiments of the catheter have a shaft length of about 47 to 55.2 inches (120 to 140 cm). In a particular embodiment, catheter 8 has a shaft length of about 47.24±0.200 inches (about 120±0.5 cm).

In the embodiment of FIG. 1, the inner diameter of catheter body 9 is about 0.040±0.004 inches (about 1.02±0.102 mm) at the distal end of wire braid layer 14 and is about 0.035±0.004 inches (0.89±0.102 mm) at the distal tip of the catheter (i.e. at or about end opening 21). The outer diameter of catheter 8 is about 0.063±0.004 inches (1.6±0.102 mm) at the distal end of wire braid layer 14. The distance from the proximal end of marker band 16a to the distal tip of the catheter is about 0.587±0.294 inches (14.91±7.46 mm). The distance from the distal end of side-port 13 to the distal tip of the catheter is about 0.332±0.166 inches (8.43±4.21 mm).

Some embodiments of the catheter may be used with a guide-wire with a 0.035 inch (0.89 mm) outer diameter (OD), in a 6F introducer sheath with an inner diameter of about 0.079 inches (about 2 mm) When the embodiment of catheter 8 of FIG. 1 is used with a 0.035 inch (0.89 mm) guide-wire, the inner diameter of about 0.035±0.004 inches (0.89±0.102 mm) at end opening 21 will provide a close or tight fit to the guide-wire. The relatively larger inner diameter of about 0.040±0.004 inches (about 1.02±0.102 mm) at the distal end of wire braid layer 14 will provide for trackability over the guide-wire as the larger diameter provides for space around wire 19, which reduces friction and binding.

Figure 2:
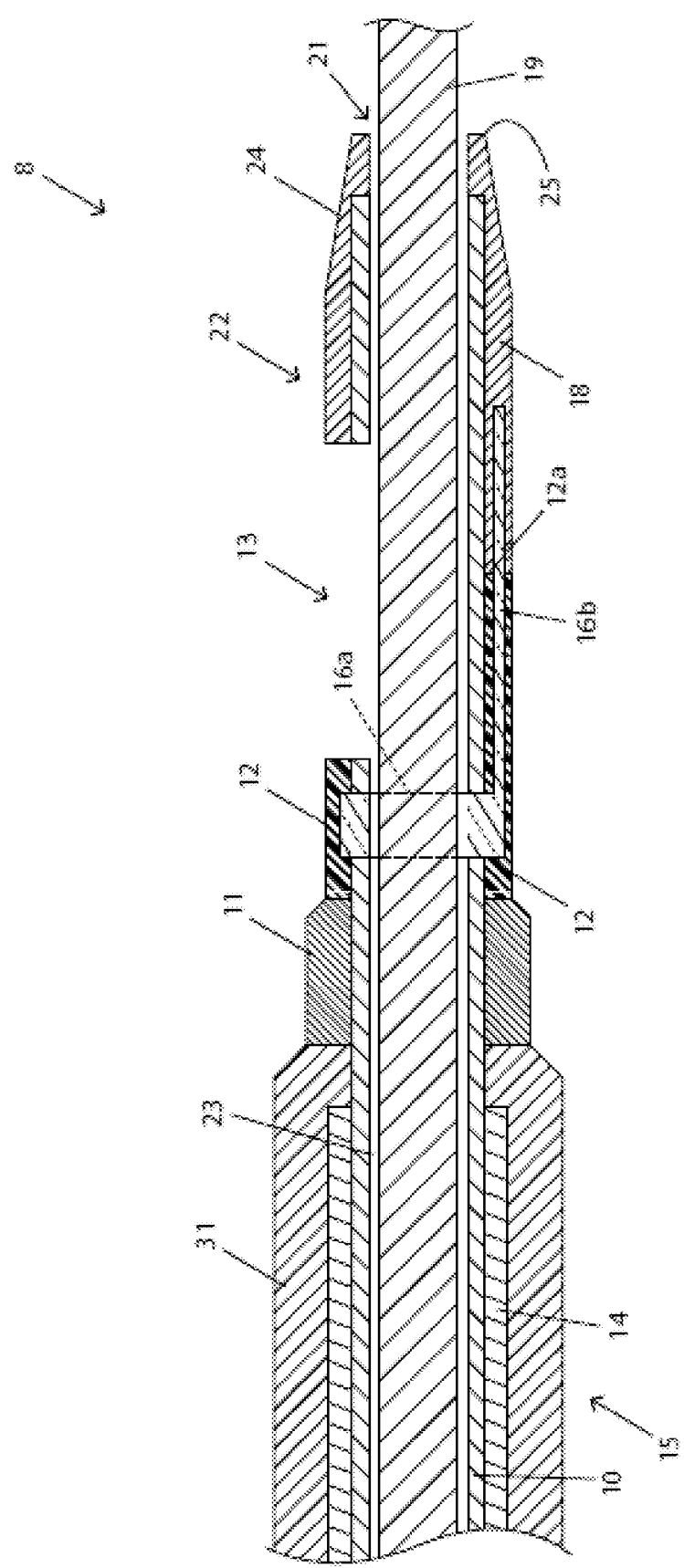
FIG. 2 is a diagrammatic cut away view of a distal portion of another embodiment of the catheter with a wire contained therein.

FIG. 2 a diagrammatic cut away view of a distal portion of the disclosed catheter illustrating materials of an embodiment of the device. The example of FIG. 2 comprises a braided shaft 15 including a wire braid layer 14. The distal end of braided shaft 15 is proximal of side-port 13. In typical embodiments, wire braid layer 14 is comprised of a metal, for example, stainless steel or Nitinol. Alternative embodiments of wire braid layer 14 are comprised of a polymer such as, for example, nylon, Teflon®, or carbon based thread. Wire braid layer 14 is covered by proximal sleeve 31, which in typical embodiments is a polymer, such as, for example, Pebax® (a thermoplastic elastomer) or another type of nylon. In the embodiments of FIG. 2, a Pebax layer 11 extends distally of braided shaft 15 and ends proximal of side-port 13. The distal end of Pebax layer 11 abuts Grilamid® layer 12, which extends distally to Grilamid distal end 12a. Grilamid distal end 12a is between the proximal and distal ends of side-port 13 such that there is a transition in the material comprising catheter body 9 from Grilamid layer 12 to nylon layer 18 at the side-port. Grilamid® is a plastic comprising a polyamide, and is also known as "polyamide 12", and as "nylon 12".

In some alternative embodiments, Pebax layer 11 is replaced by another polymer, for example, another type of nylon. In some other alternative embodiments, Grilamid layer 12 is replaced by another polymer, for example, Pebax or another type of nylon.

The embodiment of FIG. 2 also illustrates a polytetrafluoroethylene (PTFE) liner extending substantially the entire length of lumen 23 (a primary catheter lumen) to facilitate travel over a guide-wire. PTFE liner 10 has a substantially constant thickness of about 0.0013±0.0005 inches (0.0330±0.0127 mm), and in comparison to nylon layer 18 and Grilamid layer 12, is relatively flexible (it has modulus of elasticity typically ranging from about 0.39 to 0.6 gigapascals (GPa)), whereby it does not have a substantially significant effect on the rigidity of catheter 8.

Embodiments of the catheter are operable to passively collapse or deform distal of the side-port 13, as described above, as well as being operable to be advanced over a wire without compromising integrity and without experiencing ovalization. Avoidance of ovalization is achieved, for example, by distal portion 22 being configured to be sufficiently axially stiff (i.e. having sufficient column strength) to be advanceable (for example, over a guide-wire) while still being sufficiently radially flexible to be passively collapsible. To satisfy the requirements of axial stiffness and radial flexibility, the distal portion of the catheter (distal of the side-port) comprises a layer of material (nylon layer 18) that is stiff enough to provide adequate column strength and, in the disclosed embodiments, is thin enough to provide collapsibility.

Referring to the embodiments of FIGS. 1 and 2, nylon layer 18, which forms a significant part of distal portion 22, is typically a VESTAMID® nylon having stiffness (a modulus of elasticity) of about 1.4±0.14 GPa. Nylon layer 18 tapers distally in thickness from about 0.0055±0.0006 inches (0.1397±0.014 mm) to about 0.002±0.0002 inches (0.0508±0.005 mm) and in outer diameter from about 0.049±0.005 inches (1.2446±0.124 mm) to about 0.042±0.004 inches (1.0668±0.107 mm) As nylon layer 18 forms an outer layer of distal portion 22, an outer diameter of nylon layer 18 is also an outer diameter of catheter 8. As previously described, in typical embodiments, nylon layer 18 is sufficiently stiff such that distal portion 22 of catheter 8 is advancable over a wire without experiencing ovalization, i.e. while retaining a substantially non-collapsed or non-deformed configuration.

In use, when a catheter 8, for example as described hereinabove, is withdrawn or retracted within a sheath after a wire is extended through side-port 13, distal portion 22 will collapse, i.e. will adopt a collapsed or deformed configuration, when force is applied against an outer surface 24 thereof, for example when the wire pushes against it, whereby, in a manner previously described, the catheter can be withdrawn or retracted without substantially retracted the wire 19 positioned therethrough. In typical embodiments, distal portion 22 is also sufficiently resilient to return to a non-collapsed or non-deformed configuration when the wire is retracted into the catheter lumen, i.e. when the force applied by the wire to the outer surface of distal portion 22 is removed.

FIG. 8 illustrates an embodiment of catheter 8 of FIG. 2 for use with a device (such as a wire 19). The catheter 8 comprises a catheter body 9 defining a lumen 23 (a primary catheter lumen), a side-port 13 in communication with the lumen 23, and a distal portion 22 of the catheter body 9 extending distal of the side-port 13. The catheter 8 contains a wire 19 that has previously been advanced through the side-port 13. The distal portion 22 collapses radially as it passes alongside the wire 19. Catheter 8 of FIG. 8 is in a collapsed configuration inside of a sheath 20 while catheter 8 of FIG. 2 is in a non-collapsed configuration.

The embodiment of FIG. 2 further includes a marker 16 comprising radiopaque marker band 16a and marker backbone 16b which may be used to visualize the location of side-port 13 under imaging. Marker 16 is typically comprised of a radiopaque metal, for example, stainless steel, platinum, or a mixture of platinum and iridium. A proximal portion of marker 16, marker band 16a, is proximal of side-port 13 such that marker band 16a may be used for longitudinal positioning of side-port 13. Marker backbone 16b is substantially opposite to side-port 13, i.e. aligned at about 180° relative to the side-port, such that marker backbone 16b is operable to facilitate rotational positioning of side-port 13. Marker backbone 16b may also be used for longitudinal positioning.

In the embodiment of FIG. 2, there is a transition in material at or about a location of the side-port 13. Marker backbone 16b extends from marker band 16a (which is proximal of side-port 13) to a location distal of the side-port 13 thereby providing support to catheter body 9 to compensate, at least in part, for structural weaknesses caused by the side-port and transition of material at that location. Furthermore, Grilamid® layer 12 is stiffer than both Pebax® layer 11 and nylon layer 18, thereby providing further support to catheter body 9 proximally of the side-port 13, as well as to a portion of the catheter body located at a proximal portion of the side-port 13 itself i.e. Grilamid layer 12 functions as a support layer. Marker backbone 16b is positioned or embedded in catheter body 9 substantially opposite to side-port 13 and, in some embodiments, extends somewhat distally beyond the side-port 13 while avoiding interfering with (i.e. reducing) the collapsibility of distal portion 22 of catheter body 9.

FIG. 3 is an enlarged side cutaway view of marker 16. In the particular illustrated embodiment, the length of marker 16 is about 0.256±0.026 inches (6.50±0.066 mm), the length of marker backbone 16b is about 0.216±0.022 inches (5.48±0.559 mm), the thickness of marker backbone 16b is about 0.010±0.001 inches (0.25±0.03 mm), the length of marker band 16a is about 0.040±0.004 inches (about 1.02±0.102 mm), and the outer diameter of marker band 16a is about 0.050±0.005 inches (1.27±0.13 mm) In some alternative embodiments, the length of the length of marker backbone 16b is about 0.235±0.022 inches (5.07±0.559 mm).

FIG. 4 shows an end cutaway or cross-sectional view of the marker of FIG. 3 through marker band 16a, which has an outer diameter of about 0.050±0.005 inches (1.27±0.13 mm) and an inner diameter of about 0.044±0.004 inches (1.12±0.11 mm). In some alternative embodiments, marker band 16a has an outer diameter of about 0.052±0.005 inches (1.32±0.13 mm) and an inner diameter of about 0.046±0.004 inches (1.17±0.11 mm).

FIG. 5 illustrates a cross-sectional view of a sheath 20 containing a catheter body 9 and a wire 19 extending through a side-port (not shown) of the catheter. Typical embodiments of a catheter body 9 have a substantially circular cross sectional shape, and a substantially constant wall thickness, when the catheter is not bent or distorted. Some alternative embodiments have a non-circular cross sectional shape.

Figure 6A:
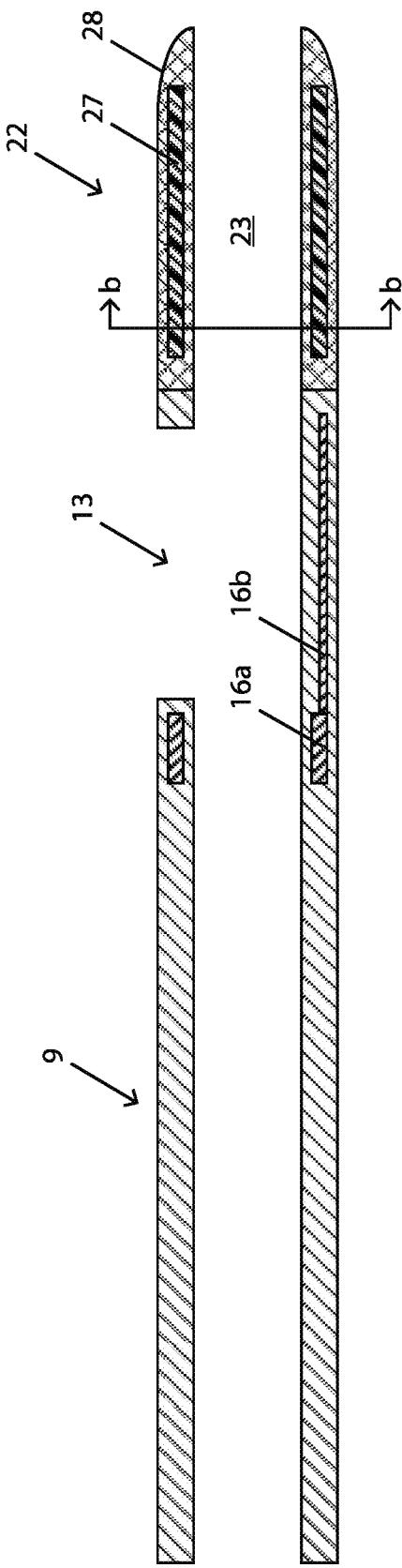
FIG. 6*a* is a side cutaway view of an alternative embodiment of the catheter having elongate support members.

FIG. 6a is a side cutaway view of an alternative embodiment of catheter body 9 having elongate support members 27 in distal portion 22. Such embodiments of the catheter comprise at least two elongate support members 27 for providing longitudinal support while allowing the distal portion to still be collapsible or inwardly deformable. In typical embodiments, elongate support members 27 are comprised of a metal, but alternative embodiments could be comprised of other materials having the appropriate support strength.

Figure 6B:
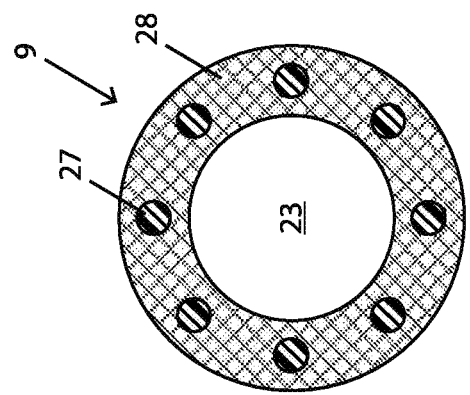
FIG. 6*b* is a cross-sectional view of the embodiment of FIG. 6*a*.

FIG. 6b is a cross-sectional view of the embodiment of FIG. 6a at cut-away line bb illustrating the elongate support members 27 arranged in a substantially circular configuration surrounding the primary catheter lumen, lumen 23. In some embodiments, polymer 28 is comprised of a biocompatible stretchable polymer, for example, silicone elastomers or polydimethylsiloxane (PDMS). The polymer can be thinner and more deformable relative to an embodiment without elongate support members 27 since the elongate support members are providing column strength. Some embodiments further comprise a radiopaque material which coats elongate support members 27.

In some alternative embodiments of catheter 8, distal portion 22 of catheter body 9 is operable to collapse inwardly into the primary catheter lumen (lumen 23) and thereby temporarily adopt a reduced profile in a collapsed configuration when a controlled force is applied to the distal portion of the catheter body. FIG. 7 is a side cutaway view of such an embodiment, wherein catheter body 9 has a shape memory element 29. Shape memory element 29 can comprise any appropriate structure, for example, a stent or a coil, wherein the shape memory element is configured to produce said controlled force when heated. Wire 30 connects shape memory element 29 to a source of heat. Some embodiments further comprise a radiopaque material coating the shape memory element. In some such embodiments, polymer 28 of the distal portion comprises a biocompatible stretchable polymer.

Some alternative embodiments of catheter 8 having a shape memory element 29 include a distal portion 22 which comprises a shape memory element 29, wherein the shape memory element is configured to expand and produce an expanding force in distal portion 22 when heated, whereby the distal portion expands (i.e. adapts an expanded configuration) to thereby allow advancement of the distal portion over a guide-wire. In such embodiments, distal portion 22 of catheter body 9 is operable to collapse inwardly into the primary catheter lumen when shape memory element 29 not heated, thereby adopting a reduced profile in a collapsed configuration.

Embodiments of the present invention may be used, for example, when withdrawing or retracting a re-entry catheter (either through a lumen or through tissue) having a wire positioned through a side-port of the catheter (into a true vessel lumen) or when withdrawing a bifurcation catheter having a wire positioned through a side-port of the catheter (into a branch artery or vein).

One embodiment of the invention is for a method of using the catheter of FIG. 1 or 2, wherein distal portion 22 has an outer diameter which tapers from about 0.049±0.005 inches (1.2446±0.124 mm) to about 0.042±0.004 inches (1.0668±0.107 mm), and the catheter is used with a guide-wire with a 0.035 inch (0.89 mm) outer diameter and a 6F introducer sheath (with an inner diameter of about 0.079 inches or about 2 mm), wherein the method comprises withdrawing the catheter from the sheath with the guide-wire extending through the side-port.

EXAMPLES

Example 1

A catheter comprising a catheter body, the catheter body defining at least a primary catheter lumen and at least one side-port in communication with the primary catheter lumen, and a distal portion of the catheter extending distal to the at least one side-port, the side-port being configured to allow travel of a device (a wire or other component) therethrough, wherein the distal portion of the catheter is radially collapsible.

Example 2

The catheter of example 1, wherein the distal portion of the catheter body is operable to collapse inwardly into the primary catheter lumen and thereby temporarily adopt a reduced profile in a collapsed configuration when force is applied to an outer surface of the distal portion of the catheter body.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A catheter for use with an elongate device, the catheter comprising a catheter body, the catheter body having a wall which defines at least a primary catheter lumen and at least one side-port in communication with the primary catheter lumen, a distal portion of the catheter body extending distal of the at least one side-port with the primary catheter lumen extending to a distal end portion of the catheter body, the wall of the distal portion of the wall of the catheter body being asymmetrically radially collapsible from the side-port to the distal end of the catheter body, the side-port being configured to allow travel of the elongate device therethrough, wherein, if the catheter is retracted while maintaining the elongate device being positioned through the side-port, the catheter is configured such that the wall of a side of the distal portion which is on the same side of the catheter which has the side-port is able to collapse radially if the elongate device pushes against an outer surface of the distal portion while another side of the distal portion opposite to the side-port retains a non-collapsed configuration wherein the distal portion of the catheter body is operable to collapse inwardly into the primary catheter lumen from the side-port to the distal end of the catheter body and thereby temporarily adopt a reduced profile in a collapsed configuration as the catheter is retracted with the device positioned through the side-port.

2. The catheter of claim 1, wherein the distal portion of the catheter comprises a layer of material which is operable to be advanced over a elongate device substantially without ovalization of the distal portion of the catheter body and which is further operable to be radially collapsible as the catheter is retracted with the elongate device positioned through the side-port.

3. The catheter of claim 2, wherein the layer of material comprises a flexible nylon layer having a stiffness of about 1.4±0.14 GPa.

4. The catheter of claim 3, wherein the flexible nylon layer of the distal portion tapers distally in thickness.

5. The catheter of claim 3, wherein the flexible nylon layer of the distal portion has an outer diameter which tapers distally.

6. The catheter of claim 3, wherein the catheter body comprises a support layer with a proximal end proximal of the side-port and a distal end at the side-port.

7. The catheter of claim 6, wherein the support layer is a plastic which is stiffer than the flexible nylon layer.

8. The catheter of claim 7, wherein the plastic is a polyamide 12.

9. The catheter of claim 1, wherein the side-port is located in a recess in an outer surface of the catheter.

10. The catheter of claim 1, further comprising a visualization marker having a marker backbone located substantially parallel and opposite to the side-port, wherein the marker backbone is operable to facilitate rotational positioning of the catheter.

11. The catheter of claim 10, wherein the marker backbone is comprised of a metal, whereby the marker backbone provides support to the catheter body.

12. The catheter of claim 11, wherein the marker backbone extends from proximal of the side-port to a location distal of the side-port, thereby providing support to the catheter body at a location of the side-port.

13. The catheter of claim 1, wherein a distal tip of the catheter body defines an end opening whereby the catheter is operable to be advanced over a elongate device as an over-the-wire device.

* * * * *